United States Patent [19]

Mitchell

[11] Patent Number: 4,638,103

[45] Date of Patent: Jan. 20, 1987

[54] PREPARATION OF DELTA-TERPINEOL

[75] Inventor: Peter W. D. Mitchell, Freehold, N.J.

[73] Assignee: Union Camp Corporation, Wayne, N.J.

[21] Appl. No.: 782,646

[22] Filed: Oct. 1, 1985

[51] Int. Cl.[4] .............................................. C07C 35/18
[52] U.S. Cl. .................................... 568/827; 568/825; 568/826
[58] Field of Search ................. 568/827, 826, 828, 825

[56] References Cited

U.S. PATENT DOCUMENTS

| | | | |
|---|---|---|---|
| 4,306,099 | 12/1981 | Fetizon et al. | 568/827 |
| 4,496,776 | 1/1985 | Edwards et al. | 568/827 |
| 4,570,022 | 2/1986 | Mitchell | 568/827 |

OTHER PUBLICATIONS

Mitzner, "J. Organic Chem." vol. 31 (1966) pp. 2022-2023 and 2419-2420.
Paul et al. "J. Amer. Chem. Soc." vol. 78 (1959) pp. 116-120.
Wilson et al. "J. Amer. Chem. Soc." vol. 101 (1979) pp. 3340-3344.
J. Sci. Hiroshima Univ., Ser. A, 18(2) (1954).

*Primary Examiner*—Werren B. Lone
*Attorney, Agent, or Firm*—Kane, Dalsimer, Kane, Sullivan and Kurucz

[57] ABSTRACT

A method of preparing delta-terpineol by reacting 1,8-cineole with an alkali metal aryl compound resulting in an E2 elimination reaction of 1,8-cineole.

6 Claims, No Drawings

PREPARATION OF DELTA-TERPINEOL

BACKGROUND OF THE INVENTION

1. FIELD OF THE INVENTION

The invention relates to a method for the preparation of α,α-dimethyl-4-methylene-cyclohexanemethanol (referred to hereafter as delta-terpineol), cis-beta-terpineol, and intermediates thereof.

2. BRIEF DESCRIPTION OF THE PRIOR ACT

Delta-Terpineol is a component of a number of essential oils, including juniper, sage, rosemary, and Scotch spearmint. Nevertheless, it is the least-known and most difficult to obtain of the four isomeric terpene alcohols known as terpineols. These four alcohols result from the hydration of turpentine or its major constituent, alpha-pinene or from the dehydration of terpin hydrate, as shown in Scheme I.

SCHEME I

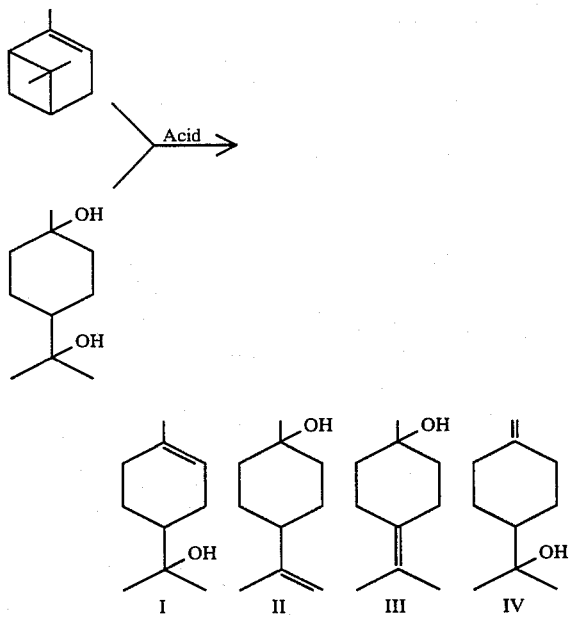

Mixtures of these alcohols and various terpene hydrocarbons are called "pine oils" and are major items of commerce. A typical pine oil from turpentine consists mainly of alpha-terpineol (I) with about 3% cis-beta-terpineol (IIa), 1% trans-beta-terpineol (IIb), and 0.5% delta-terpineol (V). Dehydration of terpin hydrate affords a pine oil with about 25% cis-and trans-beta-terpineols, about 16% gamma-terpineol (III), and about 1% delta-terpineol. Thus, of the four terpineols, only the alpha-isomer is available in quantity and in good purity. Beta-terpineol of up to 60–70% purity can be obtained by careful fractionation of the terpin dehydration reaction mixture but it invariably contains 20–30% of 3-terpinen-1-ol which has nearly the same boiling point as the cis-beta-isomer. Delta-terpineol cannot be obtained in good purity in this fashion because it occurs in such a low concentration in the crude terpineols mixture and has nearly the same boiling point as the trans-beta-isomer.

Development of the use of delta-terpineol in fragrances and synthetic essential oils has not been possible due to the lack of a commercially viable preparation. It has been synthesized by three laboratory routes [*J. Indian Chem. Soc.*, 44 (5), 388–390 (1967); *J. Org. Chem.*, 31, 2022 (1966); and *J. Amer. Chem. Soc.*, 101, 3340 (1979)], but two require exotic starting materials and expensive reagents. Only one preparation uses commerical turpentine as the ultimate feedstock but the overall yield of this multi-step procedure is less than 2 molar %.

The procedure of the present invention has three major advantages over the prior art. First, it is a single step process. Second, it proceeds in good selectivity to the desired delta-isomer; little or no trans-beta-terpineol or terpinen-1-ol is produced. Third, it uses 1,8-Cineole (eucalyptol) as its starting material. 1,8-cineole is widely available from natural sources, especially the essential oil of Eucalyptus globulus and from turpentine as a by-product of commercial pine oil production. The procedure of the invention has a further advantage in that it produces high purity cis-beta-terpineol as the only major co-product.

Cleavage of the ether bond of 1,8-cineole is well known to occur in the presence of acids. This reaction is very similar to the reactions of Scheme I and the product of such cleavage is again largely alpha-terpineol. Base-induced isomerization of 1,8-cineole has been attempted [*J. Sci. Hiroshima Univ., Ser.A*, 18 (2), (1954)] but no reaction was observed even after 60 hours at 160° C. Treatment with sodium peroxide did succeed in isomerizing 1,8-cineole, but the conversion was at best 20% and the only product observed was the alpha-terpineol isomer.

SUMMARY OF THE INVENTION

The invention comprises a method of preparing delta-terpineol which comprises; an E2 elimination of 1,8-cineole wherein the elimination reagent is an alkali metal aryl compound.

DETAILED DESCRIPTION OF THE PREFERRED EMBODIMENTS OF THE INVENTION

The method of the invention is carried out by opening of the ether bridge on the 1,8-cineole molecule. The reaction, an E2 elimination, may be effected by reacting the 1,8-cineole with an elimination reagent. Representative of elimination reagents are alkali metal alkyls, aryls, hydrides and amides. The term "alkali metal" as used herein means lithium, sodium, potassium, rubidium and cesium.

Preferred elimination agents are the alkali metal aryl compounds. The term "aryl" as used herein means the moiety obtained by removing a hydrogen atom from a parent monocyclic or polycyclic aromatic hydrocarbon, or from a substituted aromatic hydrocarbon. Representative of aryl are phenyl, tolyl, xylyl, p-phenoxyphenyl, biphenyl, p-terphenyl, naphthyl, anthryl, phenanthryl, and pyrenyl.

Preferred elimination agents are then represented by alkali metal aryls such as phenyl lithium, tolyl sodium, naphthyl sodium and equivalent alkali metal aryls.

Alkali metal aryl compounds may be prepared by many known methods, for example, reaction of an aryl halide with an alkali metal as described in Pines and Stalick, "Base-Catalyzed Reactions of Hydrocarbons and Related Compounds," Academic Press, 1977. Another method is direct reaction of certain polycylic aromatic hydrocarbons with the metal. Details of the reactions of sodium metal with naphthalene, anthracene, and phenanthrene, for example, were reported by Paul, Lipkin, and Weissman; see *J. Amer. Chem. Soc.*, 78, 116 (1956).

The most preferred elimination agent is the material obtained by reacting sodium metal and anthracene. The structure of this material is not exactly characterized but can be represented by the formulae:

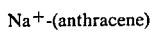

or

The method of the invention may be carried out by simple admixture of the 1,8-cineole with the elimination reagent. The reaction may be represented schematically by the formulae in Scheme II, where sodium-anthracene is shown as illustrative of the elimination agent.

SCHEME II

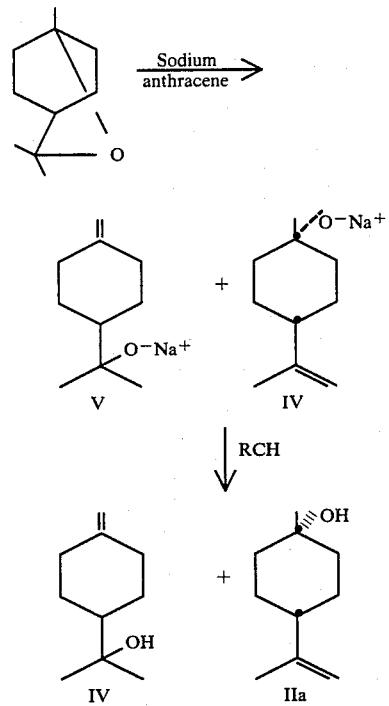

+ dihydro-anthracene

The sodium salts (V) and (VI) are formed as intermediates in the ratio of about 2 to 1 depending on the reaction conditions. It is important to control the reaction time at temperature so as not to allow these intermediates to isomerize to the sodium salts of alpha - and gamma-terpineol. Thus, the reaction is advantageously monitored by gas chromatography and water (R=H) an acid, or an alcohol (R=alkyl), for example, isopropanol, added to the reaction mixture when the yield of V and VI is at a maximum. This addition stops the reaction immediately and provides the free alcohols, IV and IIa.

During the course of the reaction, the dihydro-anthracene converts to anthracene, with the loss of a molecule of hydrogen, and the anthracene reacts with further amounts of sodium. The anthracene, then, acts as a true catalyst. At the end of the reaction it is recovered along with dihydro-anthracene and the mixture can be re-used.

Sodium metal itself is not an effective elimination reagent. Although the desired elimination reaction may be carried out by simple admixture of the reactants, a solvent for the elimination agent may be added to the reaction mixture. Advantageously the solvent is an inert hydrocarbon, for example, toluene, xylene, heptane, spirits, and the like.

Alternately, the solvent can be the terpenic materials associated with 1,8-cineole during its isolation production from alpha-pinene especially the pinenes and para-menthadienes.

Although temperature and pressure are not critical, the above-described reaction proceeds advantageously at a temperature within the range of from about 50° to 250° C., preferably 90°-180° C.

The proportions of reactants employed in the method of the invention are also not critical, stoichiometric proportions of the alkali metal being acceptable. Preferably a small excess of the elimination reagent is employed. In the preferred embodiment of the invention, the anthracene catalyst is employed in the proportion 1-100% by weight on the 1,8-cineole. The most preferred amount is 5-60% by weight of the 1,8-cineole.

The reaction is conveniently carried out in conventional reaction apparatus. Progress of the reaction may be followed employing known analytical technique. In general the reaction is complete within 1 to 36 hours. Upon termination of the reaction, the desired delta-terpineol may be separated from the reaction mixture by conventional techniques such as by distillation. Any unconverted 1,8-cineole is readily recovered by distillation.

The following examples describe the manner and process of making and using the invention and set forth the best mode of carrying out the invention but are not to be construed as limiting.

EXAMPLES

EXAMPLE 1

A mixture of sodium metal (0.6 g), anthracene (0.3 g), 1,8-cineole (3.4 g of 99% purity), and limonene (10 g) was stirred under a nitrogen atmosphere and heated to reflux, about 75° C. After 4.5 hours a sample of the reaction mixture was cooled, hydrolyzed, and analyzed by gas chromatograph. The oil contained no remaining cineole, 12.7% delta-terpineol, 6.1% cis-beta-terpineol, and 2.9% alpha+gamma-terpineols. This represents a molar yield of delta-terpineol of 53% and of cis-beta-terpineol of 25%.

EXAMPLE 2

A mixture of sodium metal (1.0 g), anthracene (0.3 g), 1,8-cineole (3.4 g of 99% purity) and dipentene (10 g) was refluxed under nitrogen for 6 hours. Water was added to the cooled mixture and the precipitated oil purified by chromatography on a column of alumina using heptane as eluent. The purified material contained by weight 57% delta-terpineol, 27% cis-beta-terpineol and 9% alpha-terpineol. The presence of delta-terpineol as the major component was confirmed by comparison of NMR and IR spectral data (FIGS. 1 & 2) with those in the literature.

EXAMPLE 3

A mixture of 1,8-cineole (3.4 g), anthracene (2.0 g), sodium (0.5 g) and tetrahydrofuran (10 g) was refluxed (67° C.) under nitrogen for 6 hours. Analysis by gas chromatography showed 12.8% conversion of the 1,8-cineole into a mixture of cis-beta-terpineol (4.0%), delta-terpineol (7.5%) and alpha-terpineol (0.4%). Thus the selectivity in an ether solvent to delta-terpineol was 58.5%.

What is claimed is:

1. A method of preparing delta-terpineol, comprising an E2 elimination reaction of 1,8-cineole, wherein the elimination reagent is an alkali metal aryl compound wherein aryl is selected from the group consisting of phenyl, tolyl, xylyl, p-phenoxyphenyl, biphenyl, p-terphenyl, naphthyl, anthryl, phenanthryl and pyrenyl.

2. The method of claim 1, wherein the alkali metal aryl is prepared by reacting an alkali metal with a polycyclic aromatic hydrocarbon.

3. The method of claim 2, wherein the alkali metal is selected from the group consisting of sodium, lithium, and potassium.

4. The method of claim 2, wherein the polycyclic aromatic compound is anthracene.

5. The method of claim 4, wherein the alkali metal is sodium.

6. The method of claim 5 wherein the reaction temperature is within the range of from about 60°–180° C. and the proportion of anthracene is between from about 5 to about 60 percent by weight of the 1-8-cineole.

* * * * *